(12) United States Patent
McNamara et al.

(10) Patent No.: US 7,430,892 B2
(45) Date of Patent: Oct. 7, 2008

(54) IMPACT HEAD AND METHOD TO SIMULATE BOX DROP IMPACT

(75) Inventors: Scott J. McNamara, Malvern, PA (US); Russell E. Fay, Newark, DE (US)

(73) Assignee: The Boeing Company, Chicago, IL (US)

( * ) Notice: Subject to any disclaimer, the term of this patent is extended or adjusted under 35 U.S.C. 154(b) by 71 days.

(21) Appl. No.: 11/543,565

(22) Filed: Oct. 5, 2006

(65) Prior Publication Data

US 2008/0110237 A1    May 15, 2008

(51) Int. Cl.
*G01M 7/00* (2006.01)

(52) U.S. Cl. .................................. 73/12.13

(58) Field of Classification Search ...... 73/12.01–12.14
See application file for complete search history.

(56) References Cited

U.S. PATENT DOCUMENTS

| 4,470,440 | A | * | 9/1984 | Thor | 144/195.5 |
| 4,545,236 | A | * | 10/1985 | Turczyn | 73/12.04 |
| 4,989,462 | A | * | 2/1991 | Davis et al. | 73/862.53 |
| 5,739,411 | A | * | 4/1998 | Lee et al. | 73/12.13 |
| 6,109,365 | A | * | 8/2000 | Lamoureux et al. | 173/90 |
| 6,523,391 | B1 | * | 2/2003 | Knox et al. | 73/12.06 |
| 7,284,414 | B2 | * | 10/2007 | Wu | 73/79 |

* cited by examiner

*Primary Examiner*—Max Noori
(74) *Attorney, Agent, or Firm*—Tung & Assoc.

(57) ABSTRACT

A method of simulating dropping of a box on an impact specimen is disclosed. An illustrative embodiment of the method includes providing an impact head simulating a corner of a box, providing an impact specimen, causing impact of the impact head with the impact specimen and examining the impact specimen. A method of simulating dropping of a box on an impact specimen is also disclosed.

20 Claims, 1 Drawing Sheet

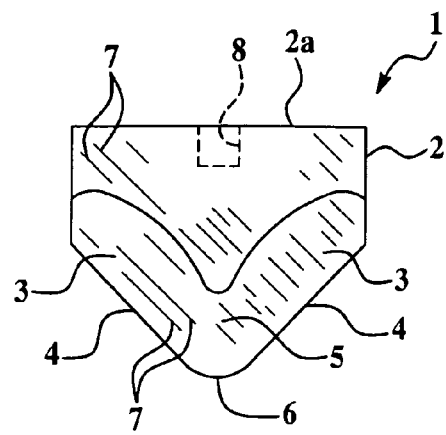
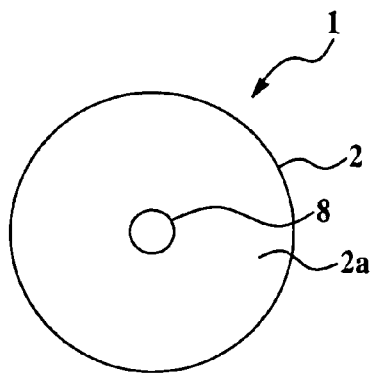
FIG. 1
FIG. 2
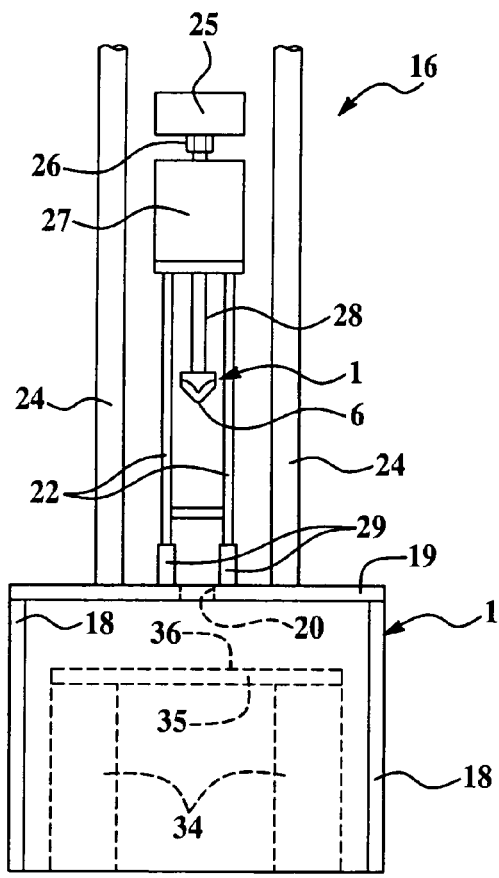
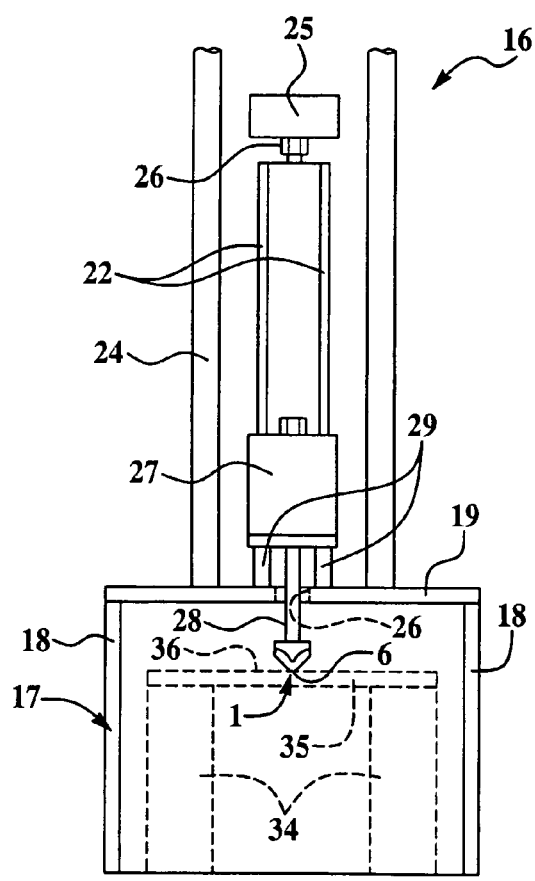
FIG. 3
FIG. 4

IMPACT HEAD AND METHOD TO SIMULATE BOX DROP IMPACT

FIELD OF THE INVENTION

The present invention relates to box drop impact tests for testing floor panels. More particularly, the present invention relates to an impact head and method which simulates impact of an edge or corner on a box against an impact specimen in a box drop impact test.

BACKGROUND OF THE INVENTION

Cargo compartment flooring in the cargo compartment of an aircraft is required to withstand certain minimum weight and drop test standards. Typically, cargo compartment flooring includes multiple floor panels which are attached to permanently installed transverse and longitudinal beams. For example, a floor panel which is 18 inches square and supported at two edges must be able to sustain, without failure, a minimum of 2,000 pounds applied over an area which is 1 inch in diameter in the center of the panel. The upper surface of the cargo compartment flooring must be adapted to support a load of 400 pounds which is applied by a ¾ inch diameter steel ball without failure or permanent indentation which is greater than 0.05 inch.

A floor panel must be sufficiently strong to withstand, without failure, impact from a sturdily-constructed pine box which is uniformly-loaded such that the box and its contents weigh 200 pounds and is dropped from a height of 13 inches above the panel (distance between the panel and the lowest corner of the box) such that one corner of the box strikes the center of the panel. A line between the center of gravity of the box and the contact point with the floor panel is vertical upon impact. The corner radius of the box cannot exceed ½ inch. The local deformation in the floor caused by the impact cannot exceed 0.3 inches. One of the limitations of the conventional box drop method for testing floor panels of aircraft cargo compartments, however, is that the method is time-consuming and expensive.

SUMMARY OF THE INVENTION

The present invention is generally directed to a method of simulating dropping of a box on an impact specimen is disclosed. An illustrative embodiment of the method includes providing an impact head simulating a corner of a box, providing an impact specimen, causing impact of the impact head with the impact specimen and examining the impact specimen.

The present invention is also generally directed to an impact head which simulates a corner of a box. An illustrative embodiment of the impact head includes an impact head base, a pair of head surfaces provided in the impact head base, a head ridge joining the pair of head surfaces and an impact point at an end of the head ridge.

BRIEF DESCRIPTION OF THE DRAWINGS

The invention will now be described, by way of example, with reference to the accompanying drawings, in which:

FIG. 1 is a side view of an impact head suitable for implementation of the invention.

FIG. 2 is a top view of the impact head.

FIG. 3 is a front view of an impact apparatus, with an illustrative embodiment of the impact head of the invention mounted on a load cell of the impact apparatus prior to impact of the impact head with an impact specimen (shown in phantom).

FIG. 4 is a front view of an impact apparatus, after impact of the impact head with the impact specimen (shown in phantom).

DETAILED DESCRIPTION OF THE INVENTION

Referring initially to FIGS. 1 and 2, an illustrative embodiment of the impact head according to the invention is generally indicated by reference numeral 1. The impact head 1 is shaped to simulate the corner of a wooden box in a box drop impact test, which will be hereinafter described. The impact head 1 is a wood such as pine, for example, and typically includes an impact head base 2 having a generally flat or planar base surface 2a. A shaft opening 8 extends into the base surface 2a. In a typical embodiment of the impact head 1, the shaft opening 8 is 0.5" in diameter. The impact head base 2 has a pair of angled or sloped head surfaces 3. The head surfaces 3 taper to join each other along a head ridge 5. The head surfaces 3 have head edges 4 which join at an impact point 6 at one end of the head ridge 5. Typically, the corner radius of the impact point 6 does not exceed about ½ inch. As shown in FIG. 1, wood grains 7 of the impact head 1 are oriented at a generally 45-degree angle with respect to the plane of the base surface 2a.

Referring next to FIGS. 3 and 4, an impact testing apparatus 16 in typical implementation of the impact head 1 is shown. The impact testing apparatus 16 may be, for example, a conventional Dynatup® impact testing apparatus. The impact testing apparatus 16 typically includes an impact platform 17 having multiple platform legs 18 and a platform panel 19 supported by the platform legs 18. A head opening 20 extends through the platform panel 19. Multiple rebound brakes 29 extend from the platform panel 19 of the impact platform 17. Rails 22 extend upwardly from the respective rebound brakes 29. An impact frame 24 extends from the impact platform 17. A release box 25 is supported by the impact frame 24 and detachably supports a weight 27 through a releasable hook 26. An elongated load cell 28 extends downwardly from the weight 27. The weight 27 is slidably mounted on the rails 22 of the impact testing apparatus 16.

In typical application of the invention, the impact head 1 is used in conjunction with the impact testing apparatus 16 to test the strength of an impact specimen 35 (shown in phantom in FIGS. 3 and 4), such as a floor panel which is to be used as flooring in a cargo compartment of an aircraft, for example. The impact head 1 is fabricated to simulate the corner of a wooden box having a selected weight in the simulated dropping of the box on the impact specimen 35 in order to test the strength of the impact specimen 35. The impact specimen 35 is typically supported beneath the platform panel 19 of the impact platform 17 on a pair of spaced-apart specimen support blocks 34. In typical application, the impact specimen 35 is 18" square. Each of the specimen support blocks 34 is 18" long and 1" wide. The impact specimen 35 is placed across the specimen support blocks 34 to simulate suspension of the impact specimen 35 between two plates in a typical box drop test.

The magnitude of the weight 27, which corresponds to the weight of a wooden box in an actual box drop test, is selected. In a typical simulated box drop test, the weight 27 is 200 lbs., although the magnitude of the weight 27 may be lesser or greater depending on the desired application of the impact head 1. The impact head 1 is attached to the load cell 28 typically by threadably inserting a threaded shaft (not shown)

provided on the load cell 28 into the shaft opening 8 of the impact head base 2. The weight 27 is supported by the release box 25 by causing engagement of the release hook 26 with the weight 27. The distance between the impact point 6 of the impact head 1 and a contact point 36 on the surface of the impact specimen 35 is typically about 13 inches. Furthermore, the impact point 6 of the impact head 1 is directly vertical with respect to the contact point 36 on the surface of the impact specimen 35.

The weight 27 is released from the release box 25 typically by lever-actuated disengagement of the release hook 26 from the weight 27. Accordingly, the weight 27 slides downwardly on the rails 22 until the impact head 1 extends through the head opening 20 in the platform panel 19 and then the impact point 6 of the impact head 1 strikes the contact point 36 on the impact specimen 35. The wood grains 7 of the impact head 1 are oriented at a generally 45-degree angle with respect to the plane of the impact specimen 35. The weight 27 is then raised on the rails 22 and re-attached to the release hook 26, after which the contact point 36 on the impact specimen 35 is examined. In applications in which the impact specimen 35 is an aircraft cargo compartment floor panel, the local deformation in the impact specimen 35 at the contact point 36 typically must not exceed 0.3 inches to pass the box drop test.

Although this invention has been described with respect to certain exemplary embodiments, it is to be understood that the specific embodiments are for purposes of illustration and not limitation, as other variations will occur to those of ordinary skill in the art.

What is claimed is:

1. A method of simulating dropping of a box on an impact specimen, comprising:
   providing an impact head simulating a corner of said box;
   providing an impact specimen;
   providing an impact testing apparatus;
   fitting said impact head on said impact testing apparatus;
   causing impact of said impact head with said impact specimen by operation of said impact testing apparatus, said operation comprising dropping said impact head on said impact specimen from a height above said impact specimen; and
   examining said impact specimen.

2. The method of claim 1 wherein said impact specimen comprises an aircraft cargo compartment floor panel.

3. The method of claim 1 wherein said impact head comprises pine wood.

4. The method of claim 1 further comprising providing a weight on said impact head, said impact head comprising an impact point having a radius simulating said corner of said box.

5. The method of claim 4 wherein said weight comprises a 200-pound weight.

6. The method of claim 1 wherein said causing impact of said impact head with said impact specimen comprises placing said impact head about 13 inches above said impact specimen and dropping said impact head on said, impact specimen, respectively.

7. The method of claim 1 wherein said impact head comprises pine wood having wood grains oriented at a generally 45-degree angle with respect to a plane of said impact specimen.

8. The method of claim 1 further comprising a generally flat surface provided on said impact specimen and a shaft opening extending into said surface, and wherein said impact testing apparatus extends into said shaft opening.

9. A method of simulating dropping of a box on an impact specimen, comprising:
   providing an impact head simulating a corner of a box, said impact head having an impact head base, a pair of head surfaces provided in said impact head base, a head ridge joining said pair of head surfaces and an impact point comprising a radius simulating a corner of said box at an end of said head ridge;
   providing an impact specimen;
   causing impact of said impact point of said impact head with said impact specimen, said impact caused by dropping said impact head on said impact specimen from a height above said impact specimen; and
   examining said impact specimen.

10. The method of claim 9 wherein said impact specimen comprises an aircraft cargo compartment floor panel.

11. The method of claim 9 wherein said impact head comprises pine wood.

12. The method of claim 9 further comprising providing a weight on said impact head.

13. The method of claim 12 wherein said weight comprises a 200-pound weight.

14. The method of claim 9 wherein said causing impact of said impact point of said impact head with said impact specimen comprises placing said impact point of said impact head about 13 inches above said impact specimen and dropping said impact head on said impact specimen, respectively.

15. The method of claim 9 wherein said impact head comprises pine wood having wood grains oriented at a generally 45-degree angle with respect to a plane of said impact specimen.

16. The method of claim 9 further comprising providing an impact testing apparatus and providing said impact head on said impact testing apparatus, and wherein said causing impact of said impact point of said impact head with said impact specimen comprises causing impact of said impact point of said impact head with said impact specimen by operation of said impact testing apparatus.

17. An impact head simulating a corner of a box dropped onto an impact specimen in an impact test, comprising:
   an impact head base;
   a pair of head surfaces provided in said impact head base; and,
   a head ridge joining said pair of head surfaces and an impact point at an end of said head ridge, wherein said impact point comprises a radius simulating a corner of said box.

18. The impact head of claim 17 wherein said impact head base, said head ridge and said impact point comprises pine wood.

19. The impact head of claim 17 further comprising a shaft opening provided in said impact head base.

20. The impact head of claim 17 further comprising a generally planar base surface provided on said impact head base and wherein wood grains in said impact head are oriented at a generally 45-degree angle with respect to said base surface.

* * * * *